(12) United States Patent
Wainwright

(10) Patent No.: US 8,181,826 B2
(45) Date of Patent: May 22, 2012

(54) SCENT SPRAYER

(76) Inventor: Thomas G. Wainwright, Westmoreland, TN (US)

( * ) Notice: Subject to any disclaimer, the term of this patent is extended or adjusted under 35 U.S.C. 154(b) by 518 days.

(21) Appl. No.: 12/458,360

(22) Filed: Jul. 9, 2009

(65) Prior Publication Data
US 2010/0096409 A1    Apr. 22, 2010

Related U.S. Application Data

(60) Provisional application No. 61/136,989, filed on Oct. 20, 2008.

(51) Int. Cl.
*B67D 7/06* (2010.01)
(52) U.S. Cl. ............ 222/181.2; 222/183; 222/192; 222/504; 222/645; 222/646; 222/649; 43/1; 43/2; 43/21.2
(58) Field of Classification Search ............. 222/181.2, 222/182–183, 180, 162, 192, 638–639, 645–646, 222/648–650, 504, 63, 402.13, 333; 43/1–2, 43/21.2; 248/161, 163.1
See application file for complete search history.

(56) References Cited

U.S. PATENT DOCUMENTS

| 4,570,824 | A |   | 2/1986  | Bolling |       |
|-----------|---|---|---------|---------|-------|
| 4,773,177 | A | * | 9/1988  | Gray et al. | 43/1 |
| 4,953,763 | A |   | 9/1990  | Kierum et al. |  |
| 5,299,376 | A |   | 4/1994  | Roberts |       |
| 5,555,663 | A | * | 9/1996  | Burgeson | 43/1 |
| 5,555,664 | A |   | 9/1996  | Shockley |      |
| 5,832,648 | A | * | 11/1998 | Malone  | 43/1 |
| 6,158,668 | A | * | 12/2000 | Burgeson | 239/47 |
| 6,241,161 | B1 |  | 6/2001  | Corbett |       |
| 6,443,434 | B1 |  | 9/2002  | Prather |       |
| 6,537,535 | B1 |  | 3/2003  | Williams |      |
| 6,655,604 | B2 |  | 12/2003 | Tuttobene, Jr. | |
| 6,983,103 | B1 |  | 1/2006  | Parcher |       |
| 7,029,362 | B1 |  | 4/2006  | Halstead |      |
| 2005/0199740 | A1 | | 9/2005 | Harris, Jr. |    |
| 2006/0169793 | A1 | | 8/2006 | Price et al. |   |
| 2007/0042012 | A1 | | 2/2007 | Ambrose, Jr. et al. | |

FOREIGN PATENT DOCUMENTS

| GB | 2 153 011 A | 8/1985 |
|----|-------------|--------|
| GB | 2 251 792 A | 7/1992 |

OTHER PUBLICATIONS

Harmon Deer Scents, 2 pages printed from the Internet, Jun. 27, 2008 http://www.harmondeerscents.com.
DOC's Persimmon Spray Bottle, 1 page printed from the Internet—Jun. 27, 2008, http://www.dickssportinggoods.com/product/index.jsp?productId=2533007.

\* cited by examiner

*Primary Examiner* — Frederick C. Nicolas
(74) *Attorney, Agent, or Firm* — Richard C. Litman

(57) ABSTRACT

The scent sprayer is a device for attracting animals. The device incorporates a scent spray dispenser. The dispenser includes an optionally camouflaged housing with a wind vane for rotating the sprayer in the direction of the wind. A radio frequency (RF) receiver is enclosed in the housing. The receiver is connected to a circuit that operates an electromechanical coupler to release a scent from the scent spray dispenser that attracts game. The scent sprayer also includes an RF transmitter that transmits a control signal on the same frequency as the RF receiver to trigger release of the scent. The scent contained in the scent spray dispenser may be urine, blood, pheromones, or any other scent suited to the game being hunted.

5 Claims, 5 Drawing Sheets

SCENT SPRAYER

CROSS-REFERENCE TO RELATED APPLICATION

This application claims the benefit of U.S. Provisional Patent Application Ser. No. 61/136,989, filed Oct. 20, 2008.

BACKGROUND OF THE INVENTION

1. Field of the Invention

The present invention relates generally to devices for attracting animals, and more specifically to a scent sprayer for attracting game animals that operates by wireless remote control.

2. Description of the Related Art

Hunters have adopted various devices for attracting the animal while allowing the hunter to remain at a distance. These devices play on the keen senses of the animal to attract the animal to the device through powerful primal signals, usually either visual or olfactory, to which the animals will respond. Many such devices use a scent to lure the animal. Various means have been developed for delivering the scent without disclosing the hunter's location. For example, one scent spray method commonly used involves spraying scent on the hunter's pants legs and the bottom heel part of his shoes. The scent is typically obtained from the urine of the animal, perhaps from a sexually active female, which therefore contains powerful pheromones attractive to the male animal. However, none of these devices have proven to be entirely satisfactory.

Thus, a scent sprayer solving the aforementioned problems is desired.

SUMMARY OF THE INVENTION

The scent sprayer is a device for attracting animals. The device incorporates a scent spray dispenser. The dispenser includes an optionally camouflaged housing with a wind vane for rotating the sprayer in the direction of the wind. A radio frequency (RF) receiver is enclosed in the housing. The receiver is connected to a circuit that operates an electromechanical coupler to release a scent from the scent spray dispenser that attracts game. The scent sprayer also includes an RF transmitter that transmits a control signal on the same frequency as the RF receiver to trigger release of the scent. The scent contained in the scent spray dispenser may be urine, blood, pheromones, or any other scent suited to the game being hunted.

A wireless remote pushbutton controls the scent sprayer. The dispenser has a hanging strap for set up in a tree, and an attachment boss for set up on a tripod. Alternatively, automatic timing mechanisms on-board the device may be employed to dispense the scent.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

As shown in FIGS. 1-5, the scent sprayer 10 is a device for attracting animals, particularly game animals being hunted, although the device may also be used by wildlife photographers, animal conservationists, naturalists, and others. The scent sprayer 10 includes an optionally camouflaged housing 25 having one or more wind vanes 40 for rotating the housing 25 in the direction of the wind. The wind vanes 40 are preferably pivotal.

Figure 1:
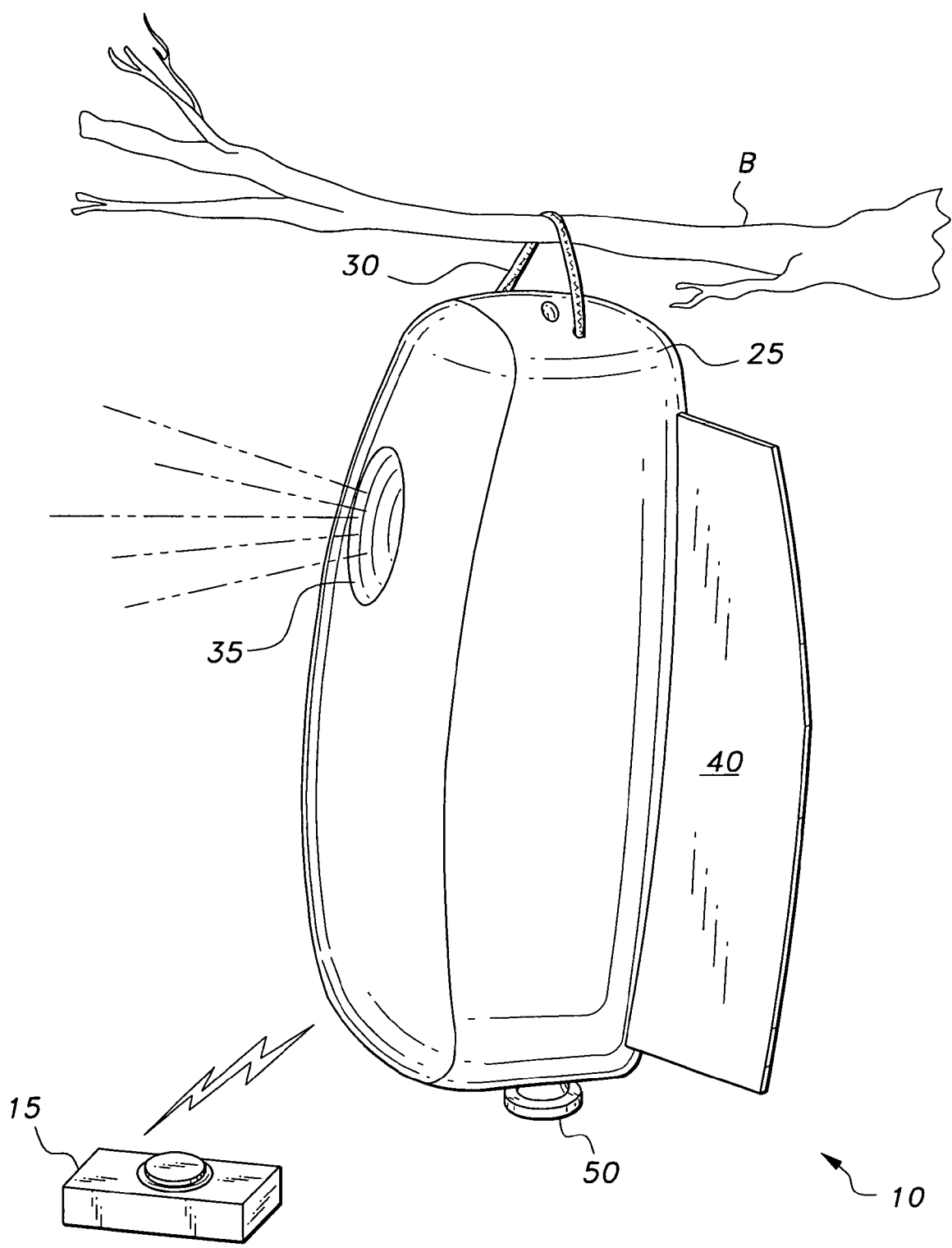
FIG. 1 is an environmental, perspective view of a scent sprayer according to the present invention.
Figure 2:
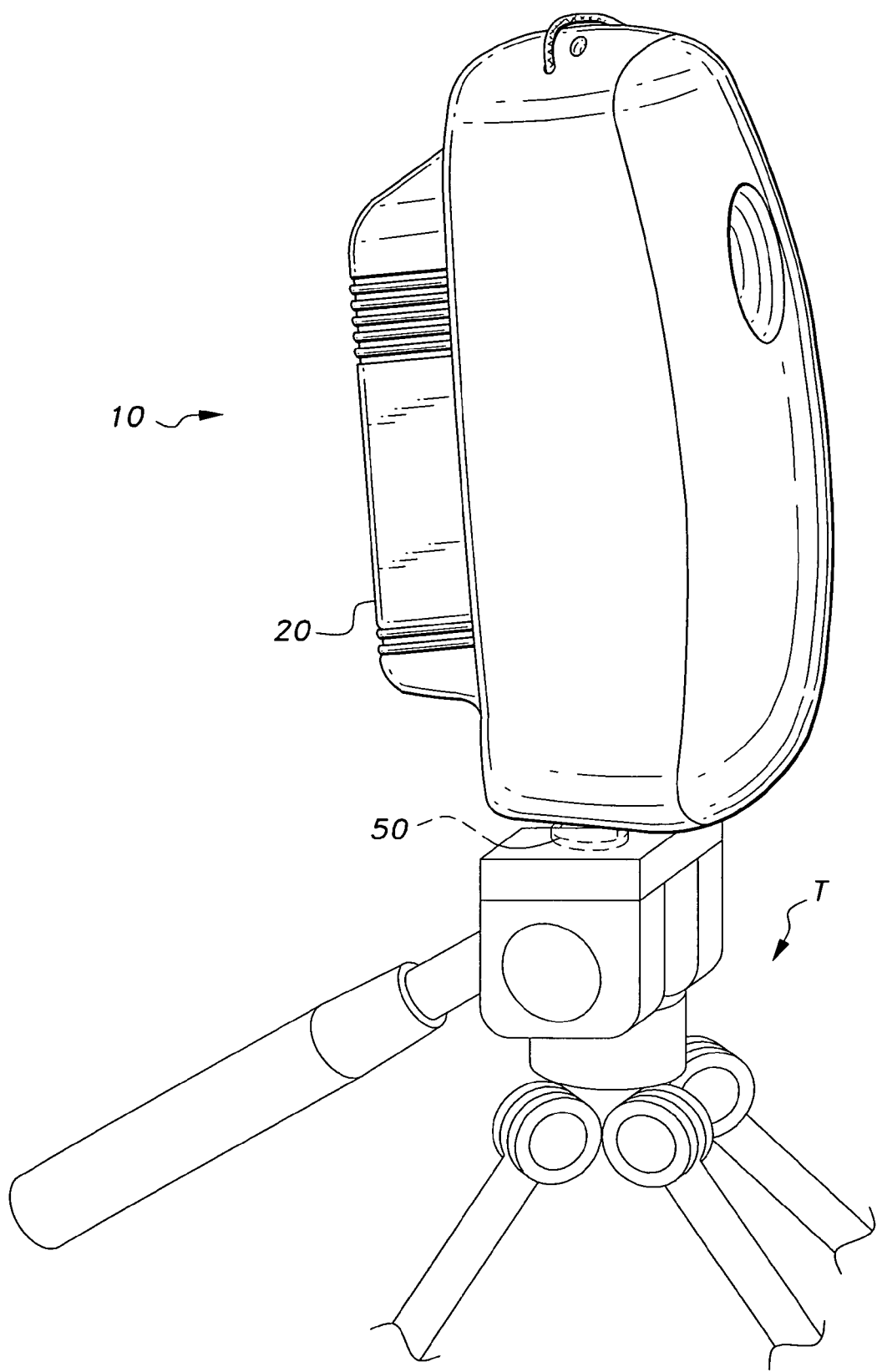
FIG. 2 is an environmental, perspective view of a scent sprayer according to the present invention attached to a tripod.

The scent sprayer has a wireless RF transmitter 15 and receiver 20 to effectuate wireless remote control of the scent sprayer 10. The housing 25 has a lanyard or hanging strap 30 for suspending the housing 25 from a tree branch B or the like, and an attachment boss 50 for set up on a tripod T (as shown in FIG. 2). Alternatively, automatic timing mechanisms on-board the device may be employed to dispense the scent as a spray in a time release manner that is electromechanically operated or controlled.

Figure 3:
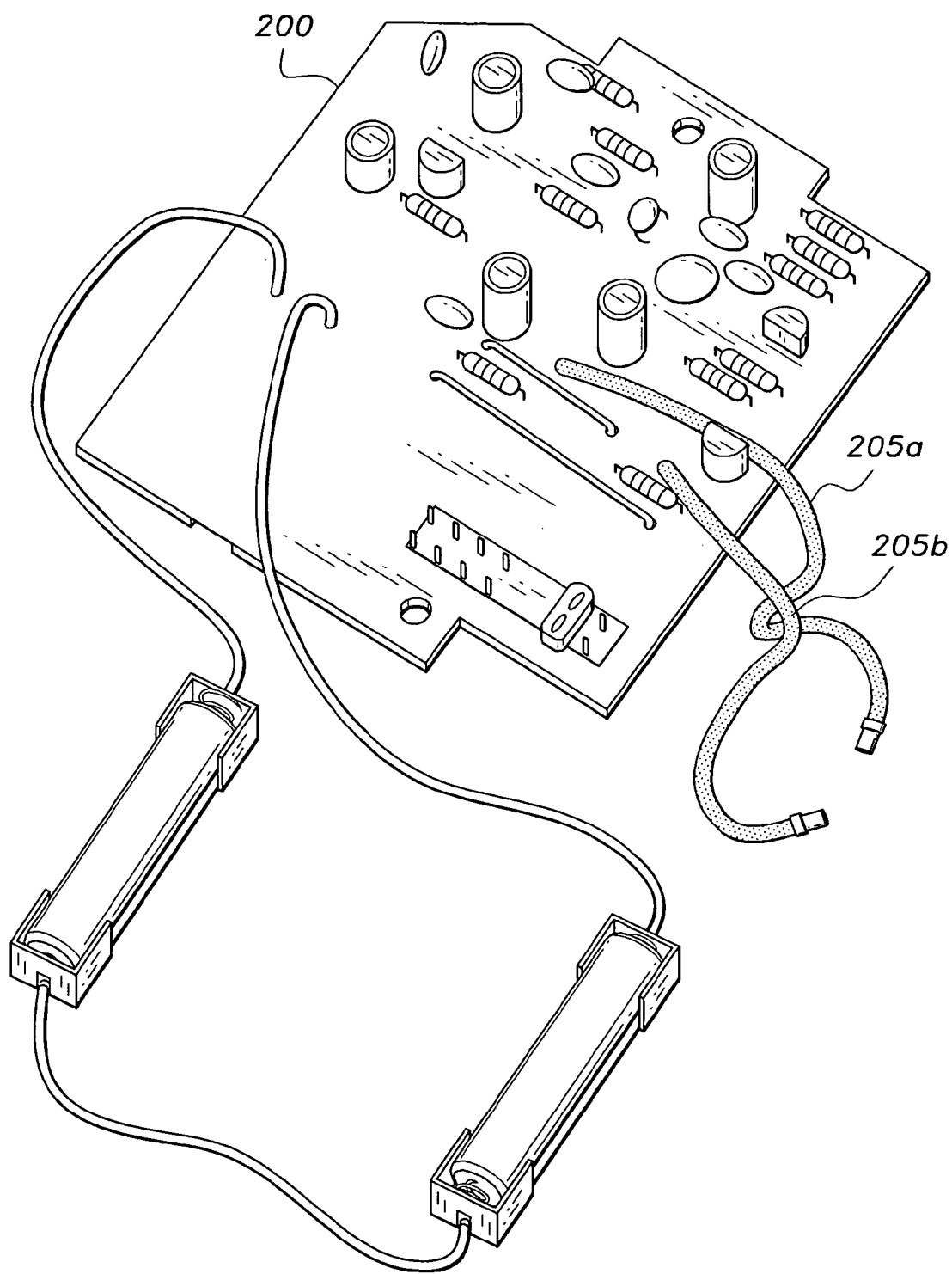
FIG. 3 is a perspective view of a circuit board utilized in a scent sprayer according to the present invention.
Figure 4:
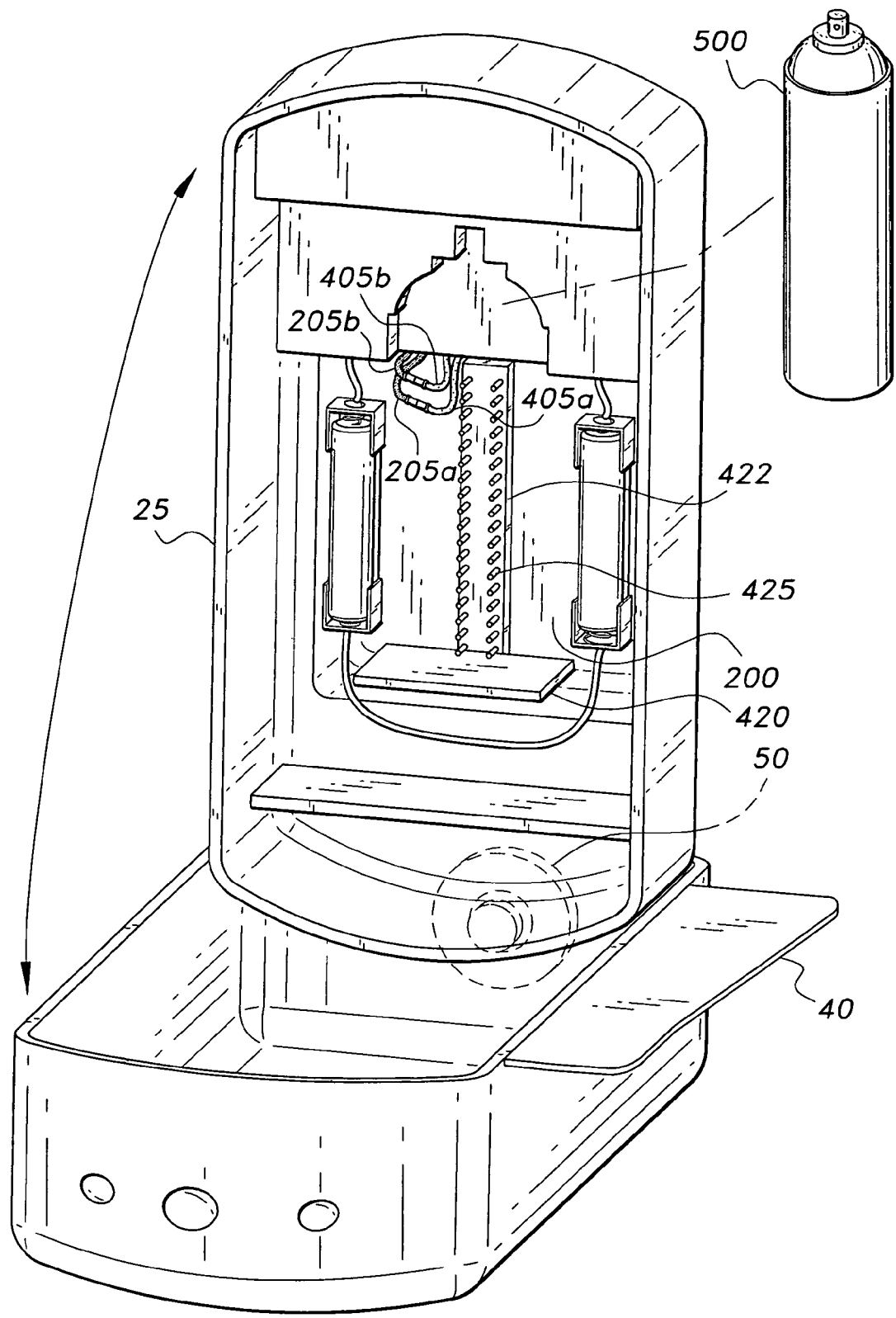
FIG. 4 is a perspective view of a scent sprayer according to the present invention, shown with the housing cover lowered.

As shown in FIGS. 3 and 4, the housing 25 encloses an RF receiver circuit mounted on a printed circuit board 200 and a container 500 containing the scent. Wires 205a and 205b conduct an output signal from the receiver circuit to another circuit that releases scent from the dispenser container 500 when the transmitter 15 is activated, e.g., by pressing the push button. When the receiver circuit 200 is actuated, current flow through the wires 205a and 205b increases significantly enough to form an actuation signal (or a voltage change forms an actuation signal) that can be routed to an electromechanical spray actuation device connected to scent container 500 by wires 405a and 405b.

A prototype of the device was constructed from a wireless doorbell, DESA specialty products model #SL-6150-RX, and an AIR WICK® FRESHMATIC® Ultra air freshener. Wires 205a and 205b are normally connected to the doorbell speaker and wires 405a and 405b are normally connected to the circuit that activates the scent container to release its contents as an aerosol spray. It is contemplated, however, that the scent sprayer 10 may be constructed by combining a wide variety of wireless receivers with a wide variety of electromechanically controlled spray dispensers to achieve the same results as achieved using the specific products named above.

As shown in FIG. 4, the scent spray container 500 can be introduced into the scent sprayer 10 when bifurcated housing 25 is swung to an open position. The container 500 is supported within the housing 25 by a can support platform 420 that can be height adjusted up and down elongate support platform riser 422, so that differently sized containers 500 may be supported within the housing 25. The elongate support platform riser 422 includes stud members 425, the stud members 425 engaging the support platform 420 to secure the support platform 420 at a user-desired height within the housing 25. Electromechanical actuation of scent sprayer 10 is designed to release a measured amount of scent product from aperture 35 of housing 25. The scent spray canister 500 may be originally manufactured with an appropriate animal scent/ pheromone, or a refill aerosol canister may be emptied of its original contents and refilled with the desired animal scent/pheromone.

Alternatively, the device may be produced by combining any type of wireless transmitter/receiver combined with any kind of electromechanically operated aerosol dispensing/spraying unit. An example of an electromechanically operated aerosol dispensing unit is described in U.S. Pat. No. 4,570,824, issued to Bolling on Feb. 18, 1986, which is incorporated by reference herein in its entirety.

Figure 5:
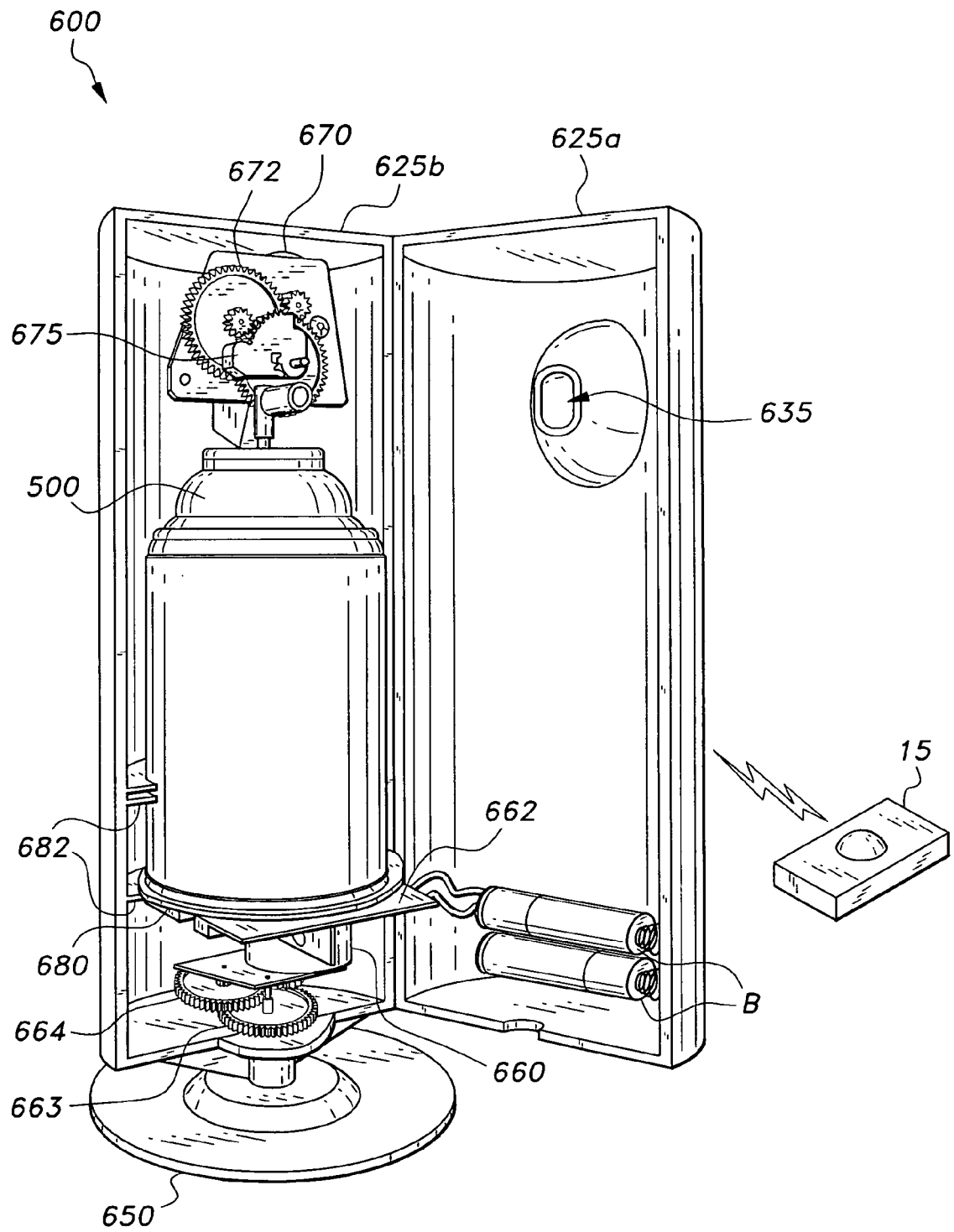
FIG. 5 is a perspective view of an alternative embodiment of a scent sprayer according to the present invention, shown with the housing cover lowered.

As shown in FIG. 5, exemplary alternative embodiment of the scent sprayer 600 has a hollow body in which body half 625b and body half 625a are pivotally connected together for ease of opening and closing the housing. Wireless receiver circuit board 662 is attached to spray can platform 680 and is also connected to batteries B. The wireless receiver circuit board 662 includes radio reception circuitry and microcontroller circuitry to respond to commands from transmitter 15. Time intervals between measured amounts of spray are preset in the microcontroller/receiver circuitry by default. However, custom delay times, i.e., interval times, may be programmed into the unit by the user. Preferably, the default time intervals between spray actuations are a pre-rut interval of 5 minutes, a rut interval of 2 minutes, and a post rut interval of 10 minutes. The spray can platform 680 is height adjustable within the unit 600 via insertion into one of platform receiving slots 682, which are spaced at vertical intervals within housing body half 625b.

Scent sprayer 600 utilizes motor 670 to operate gear 672 which meshes with toothed cam 675 to electromechanically control dispensing of spray from canister 500 through spray aperture 635, thereby achieving the same results as achieved using the specific product components of scent sprayer 10.

Unlike scent sprayer 10, scent sprayer 600 has a disk-shaped tripod mount 650, which is attached to gear 663. When the tripod mounting disk 650 is rigidly attached to a tripod, a remote control command originating from wireless transmitter 15 can actuate motor 660, which causes the motor 660 to turn gear 664, which is connected to gear 663, thereby causing the scent sprayer 600 to rotate around a central axis of mounting disk 650. This feature obviates the requirement for a wind vane 40 as found in the scent sprayer 10.

It is to be understood that the present invention is not limited to the embodiment described above, but encompasses any and all embodiments within the scope of the following claims.

I claim:

1. A scent sprayer, comprising:
a housing;
a wireless receiver having an output circuit, the wireless receiver being disposed in the housing;
a wireless transmitter having circuitry for emitting a trigger signal on a frequency identical to the wireless receiver, the trigger signal causing a change of state in the wireless receiver output circuit;
an electromechanically actuated aerosol spray container disposed in the housing, the spray container having an actuation circuit for dispensing spray from the container, the actuation circuit being electrically connected to the wireless receiver output circuit and operable to dispense a quantity of spray upon change of state of the wireless receiver output circuit;
a wind vane attached to the housing for rotating the housing according to wind direction; and
a scent disposed in the spray container, the scent emitting an odor luring animals;
whereby the spray container is adapted to be remotely triggered by the wireless transmitter to dispense a scent luring animals downwind of the housing.

2. A scent sprayer, comprising:
a housing adapted for enclosing an animal lure scent spray can;
a wireless receiver having an output circuit, the wireless receiver being disposed in the housing;
a wireless transmitter having circuitry for emitting a trigger signal and a rotation signal on a frequency identical to the wireless receiver, the wireless receiver output circuit generating a first motor actuation signal upon receiving the trigger signal and a second motor actuation signal upon receiving the rotation signal;
a first motor disposed in an upper portion of the housing, the first motor being electrically connected to the wireless receiver output circuit;
a cam operably connected to the first motor, the cam being positioned by the first motor to actuate the spray can to dispense scent in response to the motor actuation signal;
a second motor disposed in a lower portion of the housing, the second motor being electrically connected to the wireless receiver output circuit;
a disk-shaped tripod mount, the housing being rotatably mounted on the tripod mount, the housing being rotated by the second motor to change direction of scent emitted from the spray can in response to the rotation signal.

3. The scent sprayer, according to claim 2, wherein said wireless receiver output circuit includes a circuit for dispensing the scent at predetermined time intervals, the time intervals being programmable, in response to the trigger signal.

4. The scent sprayer, according to claim 2, wherein said cam has gear teeth, the scent sprayer further comprising:
a cam-operating gear engaging the gear teeth of said cam; and
a reduction gear connected to said first motor, said reduction gear driving said cam-operating gear.

5. The scent sprayer, according to claim 2, further comprising:
a tripod mount gear disposed in said housing and attached to said tripod mount;
a tripod mount reduction gear engaging the gear teeth of said tripod mount gear; said second motor rotating said tripod mount reduction gear.

* * * * *